(12) United States Patent
Van Krieken et al.

(10) Patent No.: US 9,644,218 B2
(45) Date of Patent: *May 9, 2017

(54) FERMENTATION PROCESS

(71) Applicant: PURAC BIOCHEM BV, Gorinchem (NL)

(72) Inventors: Jan Van Krieken, Gorinchem (NL); Adriaan Dirk Kon, Meerkerk (NL); André Banier De Haan, Best (NL); Frederik Gerrit Jan Kool, Leerdam (NL)

(73) Assignee: PURAC BIOCHEM BV, Gorinchem (NL)

( * ) Notice: Subject to any disclaimer, the term of this patent is extended or adjusted under 35 U.S.C. 154(b) by 215 days.

This patent is subject to a terminal disclaimer.

(21) Appl. No.: 14/395,580

(22) PCT Filed: Apr. 24, 2013

(86) PCT No.: PCT/EP2013/058500
§ 371 (c)(1),
(2) Date: Oct. 20, 2014

(87) PCT Pub. No.: WO2013/160352
PCT Pub. Date: Oct. 31, 2013

(65) Prior Publication Data
US 2015/0079647 A1 Mar. 19, 2015

Related U.S. Application Data

(60) Provisional application No. 61/637,867, filed on Apr. 25, 2012.

(30) Foreign Application Priority Data

Apr. 25, 2012 (EP) ..................................... 12165513

(51) Int. Cl.
*C12P 1/04* (2006.01)
*C12P 7/14* (2006.01)
*C12P 7/56* (2006.01)
*C12P 7/44* (2006.01)
*C12P 7/46* (2006.01)
*C12P 7/50* (2006.01)
*C12P 7/48* (2006.01)
*C12P 7/52* (2006.01)
*A61K 38/56* (2006.01)
*B01D 21/26* (2006.01)

(52) U.S. Cl.
CPC ...... *C12P 7/56* (2013.01); *C12P 7/44* (2013.01); *C12P 7/46* (2013.01); *C12P 7/48* (2013.01); *C12P 7/50* (2013.01); *C12P 7/52* (2013.01); *B01D 21/267* (2013.01); *Y02P 20/582* (2015.11)

(58) Field of Classification Search
USPC ......... 435/136, 139, 145, 132, 41, 141, 142, 435/144
IPC ............... B01D 21/267; C12P 7/46,7/56, 1/04, 7/14, 7/065, 7/44, 7/48, 7/50; A61K 38/56, 8/97
See application file for complete search history.

(56) References Cited

U.S. PATENT DOCUMENTS

| 5,236,590 A | 8/1993 | Sciamanna et al. |
| 5,506,123 A * | 4/1996 | Chieffalo .................. C12P 7/56 435/262 |
| 5,547,858 A | 8/1996 | Nagano et al. |
| 7,244,596 B2 * | 7/2007 | Baets ........................ C12P 7/56 210/723 |

FOREIGN PATENT DOCUMENTS

| EP | 2360137 A1 | 8/2011 |
| JP | H03216195 A | 9/1991 |
| WO | 2005123647 A1 | 12/2005 |
| WO | 2007079944 A1 | 7/2007 |
| WO | 2009098274 A1 | 8/2009 |
| WO | 2010063762 A2 | 6/2010 |
| WO | 2011095631 A1 | 8/2011 |
| WO | 2011159998 A2 | 12/2011 |
| WO | 2011160030 A2 | 12/2011 |

OTHER PUBLICATIONS

Bacteria—The Role of Bacteria in Fermentation Tweet http://science.jrank.org/pages/710/Bacteria-role-bacteria-in-fermentation.html>Bacteria—The Role of Bacteria in Fermentation, downloaded Jul. 16, 2016.*

(Continued)

*Primary Examiner* — Debbie K Ware
*Assistant Examiner* — Kailash C Srivastava
(74) *Attorney, Agent, or Firm* — Oliff PLC

(57) ABSTRACT

The present invention pertains to a fermentation process for the production of an organic acid salt including the steps of fermenting a microorganism in a fermentation medium in a fermentation reactor to form a fermentation broth having an organic acid salt, wherein part of the organic acid salt is present in the solid state and part of the organic acid salt is dissolved in the fermentation broth; withdrawing at least part of the fermentation broth from the fermentation reactor, providing the broth to a hydrocyclone, and withdrawing a top effluent and a bottom effluent from the hydrocyclone; providing the bottom effluent from the hydrocyclone to a solid/liquid separation step, to form a solid fraction and a liquid fraction, providing at least 30 vol. % of the total of the top effluent from the hydrocyclone and the liquid fraction from the solid-liquid separation step to the fermentation reactor.

17 Claims, 3 Drawing Sheets

OTHER PUBLICATIONS

Sep. 18, 2015 Office Action issued in Japanese Patent Application No. 2015-507518.
Habibian et al., "Application of Hydrocyclone for Removal of Yeasts from Alcohol Fermentaions Broth," Chemical Engineering Journal, vol. 138, pp. 30-34, 2008.
Jun. 19, 2013 Search Report issued in International Appliation No. PCT/EP2013/058500.
Jun. 19, 2013 Written Opinion issued in International Application No. PCT/EP2013058500.

* cited by examiner

FERMENTATION PROCESS

RELATED APPLICATIONS

The present application is a nonprovisional application of Provisional Application No. 61/637,867 filed Apr. 25, 2012 and a U.S. national stage application of PCT/EP2013/058500 filed Apr. 24, 2013.

The present invention pertains to a fermentation process for the production of an organic acid salt. The invention pertains in particular to the manufacture of lactate, succinate, and furandicarboxylic acid salts.

In the art, organic acids are often manufactured by fermentation processes. For example, fermentation processes are known for lactic acid, propionic acid, succinic acid, and acetic acid. During fermentation, base is added to keep the pH of the fermentation broth in the range appropriate for the microorganism. In consequence, the acid is often present in the fermentation broth in the form of its salt. Depending on the nature of the base, the salt may be dissolved in the fermentation broth, e.g., in the case of sodium, potassium, or ammonium salts, or it may be present in the solid form, e.g., in the case of the magnesium or calcium lactate or succinate.

Fermentations for the production of these types of compounds have been mentioned in various references.

WO2005/123647 is directed to the manufacture of lactic acid or lactate from a magnesium lactate containing medium through a SWAP-reaction in a specific pH range. The magnesium lactate may be manufactured through fermentation.

WO2010/063762 is directed to a process for manufacturing a monovalent succinate salt through a fermentation process which results in the formation of magnesium or calcium succinate, which is then converted into the monovalent salt.

WO2011/095631 is directed to a process for the manufacture of lactic acid from magnesium lactate using an electrodialysis step. It is indicated that the magnesium lactate may be obtained from a fermentation process. EP2360137 contains a similar disclosure for the manufacture of succinic acid from magnesium succinate which may be obtained through fermentation.

While these references describe how the lactate or succinate salt is processed, they contain only brief and general descriptions on how the fermentation is to be performed. It has appeared however, that it is difficult to operate a fermentation process wherein the fermentation broth comprises organic acid salt in the form of a solid product in a stable manner while obtaining a high yield of a high quality product from the overall process, especially where the process is to be carried out on an industrial scale. This problem has now been solved by the present invention.

The present invention pertains to a fermentation process for the production of an organic acid salt comprising the steps of fermenting a microorganism in a fermentation medium in a fermentation reactor to form a fermentation broth comprising an organic acid salt, wherein part of the organic acid salt is present in the solid state and part of the organic acid salt is dissolved in the fermentation broth;

withdrawing at least part of the fermentation broth from the fermentation reactor, providing said broth to a hydrocyclone, and withdrawing a top effluent and a bottom effluent from the hydrocyclone;

providing the bottom effluent from the hydrocyclone to a solid/liquid separation step, to form a solid fraction and a liquid fraction, providing at least 30 vol. % of the total of the top effluent from the hydrocyclone and the liquid fraction from the solid-liquid separation step to the fermentation reactor.

It has been found that the combination of the hydrocyclone and the provision of at least 30% of the total of the top effluent from the hydrocyclone and the liquid fraction from the solid-liquid separation step to the fermentation reactor is essential to obtaining a process which is at the same time stable, provides a product with good properties, and provides a high process yield. As is illustrated in the Examples, it is the combination of the two features which provide a stable economically feasible process yielding a product with a good impurity profile. The formation of a product with a good impurity profile is a particularly surprising feature of the present invention.

The invention will be described in detail below. The figures illustrate a number of aspects of the present invention. It should be noted, however, that the present invention is not limited by or to the embodiments illustrated therein.

Figure 1:
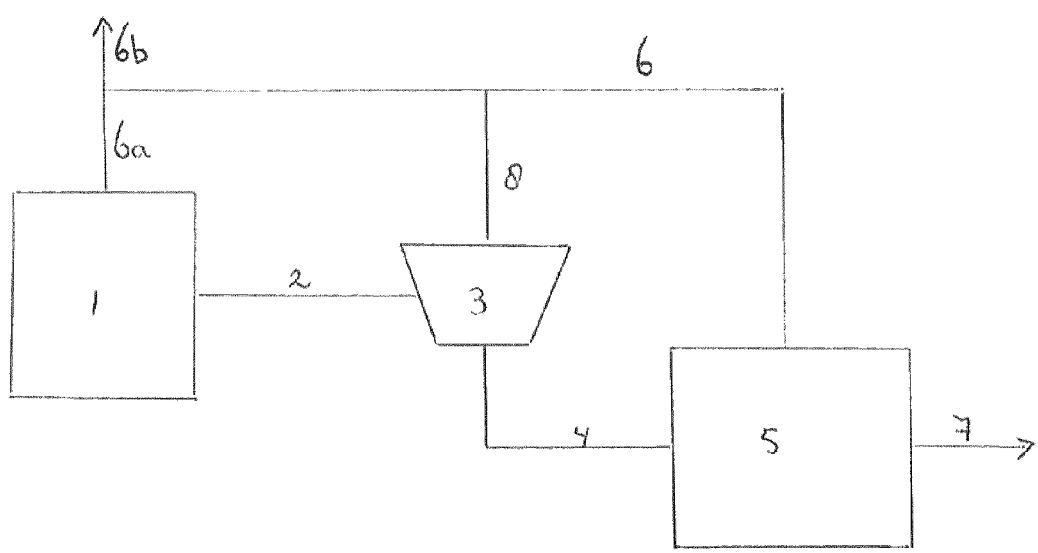
FIG. 1 illustrates a first embodiment of the present invention.

In the first step of the process according to the invention a microorganism is fermented in a fermentation medium in a fermentation reactor to form a fermentation broth comprising an organic acid salt.

The process according to the invention is applicable to fermentation processes wherein part of the organic acid salt is present in the solid state and part of the organic acid salt is dissolved in the fermentation broth. The process according to the invention is not suitable for situations where the fermentation broth does not contain organic acid salt in solid form. On the other hand, the percentage of acid salt present in solid form does not have to be high. In one embodiment, of the total amount of organic acid salt present in the medium, at least 2% is present in the solid state. More specifically, of the total amount of organic acid salt present in the fermentation medium, at least 10% is present in the solid state. In some embodiments at least 15% of the total amount of organic acid salt present in the fermentation medium is present in the solid state, or even at least 20%, or at least 30%.

On the other hand, the process according to the invention is not suitable for situations wherein all of the acid salt in the fermentation medium is present in the solid state. On the other hand, the percentage of dissolved product does not have to be high. In one embodiment, at least 5% of the total amount of acid salt present in the system is present in the dissolved state. In particular, at least 15% of the total amount of acid salt present in the system is in the dissolved state, more in particular at least 20%. As the total of the percentage of dissolved acid salt and solid acid salt is 100%, the upper limits for one of the two parameters may be derived from the lower limit for the other.

In one embodiment, the fermentation yields a fermentation broth comprising magnesium lactate wherein 50-90% of the total amount of magnesium lactate is present in the solid state (and the balance is dissolved). Within this embodiment it may be preferred for 60-85%, in particular 70-80% of the total amount of magnesium lactate to be present in the solid state (with the balance being dissolved). This embodiment may be particularly relevant for batch fermentation.

In another embodiment, the fermentation yields a fermentation broth comprising magnesium lactate wherein 10-50% of the total amount of magnesium lactate is present in the solid state (with the balance being dissolved). Within this embodiment, in may be preferred for 25-40%, in particular 20-30% of the total amount of magnesium lactate to be present in the solid state (with the balance being dissolved). This embodiment may be particularly relevant for a continuous fermentation process.

In a further embodiment, the fermentation yields a fermentation broth comprising magnesium succinate, with 10-50% of the total amount of magnesium succinate present being in the solid state (and the balance being dissolved). Preferably, 20-30% of the total amount of magnesium succinate is present in the solid state, with the balance being dissolved.

In a further embodiment, the fermentation yields calcium succinate, with 85-98% of the total amount of calcium succinate present being in the solid state (and the balance being dissolved).

The absolute amount of solid acid product in the fermentation medium as withdrawn from the reactor is not critical to the present invention. It will depend on the nature of the fermentation, and may range, e.g., between 2 and 40 wt. %, more specifically between 2 and 25 wt. %, calculated on the weight of the fermentation medium withdrawn from the reactor.

Acids of which the salts are produced manufactured via the process according to the invention are carboxylic acids, in particular carboxylic acids selected from the group consisting of mono-, di-, and tricarboxylic acids having 2-8 carbon atoms. Preferably, the carboxylic acids do not contain amino-, or amido-groups. Examples of suitable carboxylic acids include lactic acid, propionic acid, citric acid, malic acid, maleic acid, fumaric acid, adipic acid, succinic acid, itaconic acid, tartaric acid, alpha-ketoglutaric acid, oxaloacetic acid, acetic acid, acrylic acid, 2-hydroxybutyric acid, 3-hydroxypropionic acid, and furandicarboxylic acid. At this point in time fermentation processes aimed at manufacturing salts of lactic acid, succinic acid, fumaric acid, itaconic acid, adipic acid, 3-hydroxypropionic acid, and furan-dicarboxylic acid are considered preferred. Fermentation processes aimed at manufacturing lactic acid, succinic acid, or furandicarboxylic acid are considered particularly preferred. In one embodiment, the carboxylic acid is lactic acid. In another embodiment the carboxylic acid is succinic acid. In a further embodiment, the carboxylic acid is furandicarboxylic acid.

In fermentation processes of this type, the acid salt is formed through the addition of a base during the fermentation process. More specifically, in fermentations of this type the microorganism produces the carboxylic acid. The formation of acid results in a decrease in the pH. To counter this and keep the pH within the range where the microorganism can perform, a basic solution is added during the fermentation, resulting in the formation of the carboxylic acid salt. As has been explained above, the present invention pertains to the situation wherein part of the organic acid salt is present in the solid state and part of the organic acid salt is dissolved in the fermentation broth. Whether or not this is the case will depend on combination of the acid and the cation in the base, on the solubility product of the acid salt in the fermentation medium, and on the amount of product produced. It is within the scope of the skilled person using his common general knowledge, to select the base, specifically the cation in the base, in such a manner that the acid salt in the fermentation medium is present partly in the solid form and partly in the dissolved state.

Depending on the nature of the acid, suitable bases may include a cation selected from bivalent and trivalent cations, in particular bivalent cations, in particular actions selected from the group of magnesium and calcium. The use of magnesium is particularly preferred. Suitable anions for the base include oxides, hydroxides, bi- and mono-carbonates, and combinations thereof. Examples include solutions comprising one or more of calcium (hydr) oxide, calcium carbonate, calcium bicarbonate, magnesium (hydr) oxide, magnesium carbonate, and magnesium bicarbonate.

The process is believed to be of particular relevance for the manufacture of magnesium lactate, magnesium succinate, and magnesium furandicarboxylaat.

Generally, the basic solution is added in an amount effective to control the pH of the broth between about 3 and 9, more specifically between 5.5 and about 7.0. pH selection depends on the nature of the microorganism and requires no further elucidation here.

The fermentation step is otherwise carried out in a manner known in the art, and requires no further elucidation. More in particular, the nature of the carbohydrate source to be fermented is not critical, even relatively raw carbohydrate sources can be used for the fermentation. Examples of suitable carbohydrate sources are sucrose, (liquefied) starch, and glucose syrup.

Other components may be added as is conventional in the art, such as enzymes, nutrients such as nitrogen-compounds, phosphates, sulphates, vitamins, and trace elements. It is within the scope of the skilled person to select an appropriate combination of substrate, microorganism, and reaction conditions to obtain a fermentation process suitable for use in the present invention.

At least part of the fermentation broth comprising the organic acid salt is withdrawn from the reactor, and provided to a hydrocyclone, with or without intermediate processing. The fermentation broth may be withdrawn from the reactor in whole or in part, depending int. al. on whether the fermentation is a batch fermentation or a continuous fermentation. The fermentation broth as withdrawn from the reactor additionally comprises biomass and further products such as residual sugars, oligosaccharides, fermentation side products, nutrient residues, and precipitates.

If so desired, the fermentation broth may be subjected to intermediate processing. In one embodiment, the fermentation broth is provided to a gravity settler, and the heavy effluent preconcentrated slurry from the gravity settler is provided to the hydrocyclone. This embodiment may be attractive where the amount of solid acid salt in the fermentation broth is relatively limited. The light effluent from the gravity settler may be recycled back to the fermentation unit. Where the effluent from the fermentation broth contains a substantial amount of dissolved material, this is a preferred embodiment.

While intermediate processing such as the provision to a gravity settler is a possibility, the embodiment wherein at least part of the fermentation broth is provided to the hydrocyclone directly, i.e. without substantial intermediate processing, is a preferred embodiment of the present invention, as it makes the process less complicated, and reduces operating costs. It has been found that in the process according to the invention it is possible to process the fermentation broth including biomass and other contaminants as described above, while obtaining a solid product with a high purity in combination with a high overall process yield.

The fermentation broth is provided to the inlet of a hydrocyclone, whether or not after intermediate processing such as using a gravity settles as described above. A hydrocyclone is a device to classify, separate or sort particles in a liquid suspension based on the ratio of their centripetal force to fluid resistance. This ratio is high for dense and coarse particles, and low for light and fine particles. The hydrocyclone is equipped with an inlet where the feed is provided, an upper outlet and a lower outlet, which is below the upper outlet. The upper outlet is located at or near the top of the hydrocyclone; the lower outlet is located at or near the bottom of the hydrocyclone.

In the hydrocyclone a preferential separation for the solid product occurs. In general, at least 70% of the acid salt present in solid form ends up in the bottom effluent of the hydrocyclone. Preferably, at least 80% of the solid acid salt ends up in the bottom effluent, more preferably at least 85%, still more preferably at least 90%.

Of the liquid volume entering the hydrocyclone, in general at least 60% ends up in the top effluent of the hydrocyclone, preferably at least 70%. To keep the bottom effluent processable, it should contain at least some liquid volume, e.g., at least 5%, calculated on total liquid volume, or at least 8%. In general, of the liquid volume entering the hydrocyclone, at most 40% ends up in the bottom effluent of the hydrocyclone, preferably at most 30%. For the purposes of the description of the hydrocyclone separation, the liquid volume is the volume of the feed to the hydrocyclone not counting the solid acid salt particles. Other solid components such as biomass are counted within the liquid volume.

It is noted that the distribution of the biomass will generally follow the distribution of the liquid volume at least in general terms. The ranges given for the distribution of the liquid volume also apply to the distribution of the biomass.

Not wishing to be bound by theory it is believed that the hydrocyclone also contributes to the purity of the product. From the results as presented in the examples it can be seen that the use of a hydrocyclone results in a product with increased purity.

The top effluent from the hydrocyclone can be processed in various manners. In one embodiment, the top effluent is recycled back to the fermentation unit in whole or in part. If so desired, the top effluent may be subjected to a biomass removal step, e.g., through one or more of filtration, flotation, sedimentation, centrifugation, and flocculation, or to other or further purification steps. However, recycling of top effluent from the hydrocyclone in whole or in part without intermediate steps is a particular embodiment of the present invention.

To meet the requirements of the present invention that at least 30% of the total of the top effluent of the hydrocyclone and the liquid fraction from the solid-liquid separation step is recycled back to the fermentation unit, in practice generally at least 10% of the top effluent is recycled back to the fermentation unit, in particular at least 20%, more in particular at least 30%. Much higher fractions are also envisaged, e.g., at least 50%, or at least 60%. In one embodiment, the top effluent from the hydrocyclone is combined with the liquid fraction from the solid-liquid separation step before at least 30 vol. % of said combined liquid is recycled to the fermentation reactor.

The bottom effluent from the hydrocyclone is provided to a solid/liquid separation step. The solid/liquid separation step is intended to isolate the solid acid salt particles from the liquid medium containing dissolved acid salt. The solid/liquid separation step may be carried out by conventional methods like filtration, centrifugation, or sedimentation.

In a preferred embodiment, the solid/liquid separation step is carried out using a belt filter. The use of a belt filter has been found to be advantageous because it has a high wash efficiency, allowing efficient removal of biomass and solid and dissolved contaminants and obtaining a filter cake with a relatively low water content and a relatively low content of contaminant products. If so desired the belt filter can be equipped with means for washing the filter cake, e.g. in such a manner that the filter cake is reslurried, which leads to improved filterability and washing efficiency. In one embodiment, the washing liquid provided to the belt filter is a recycle stream from the belt filter. This has the advantage that washing can be effected without having to provide any additional streams to the process.

The solid fraction obtained in the solid/liquid separation step may be processed as desired, including such steps as washing. The further processing of the solid fraction is within the scope of the skilled person and does not require further elucidation here.

The liquid fraction from the solid-liquid separation step can be processed in various manners. In one embodiment, the liquid fraction from the solid-liquid separation step is recycled back to the fermentation unit in whole or in part. If so desired, the liquid fraction may be subjected to a biomass removal step, e.g., through one or more of filtration, flotation, sedimentation, centrifugation, and flocculation, or to other or further purification steps, such as evaporative cooling crystallization. However, recycling of the liquid fraction from the solid-liquid separation step in whole or in part without intermediate steps is a particular embodiment of the present invention.

In one embodiment, at least part of the liquid fraction from the solid liquid separation step is provided to a further step wherein solid acid salt is produced and isolated, e.g. a crystallizer.

In one embodiment, at least 20 vol. % of the liquid fraction from the solid-liquid separation step is recycled to the fermentation reactor, either directly or after intermediate treatment. It is preferred for this percentage to be higher, e.g., at least 30 vol. %, more in particular at least 40 vol. %. In some embodiments it may be possible to recycle a higher percentage of the liquid fraction from the solid-liquid separation step to the fermentation reactor, e.g., at least 50 vol. %, or at least 60 vol. %.

As indicated above, it is a feature of the present invention that at least 30% of the total of the top effluent from the hydrocyclone and the liquid fraction from the solid-liquid separation step is recycled to the fermentation reactor.

It is advantageous for the percentage that is provided to the fermentation reactor to be higher, e.g., at least 50%, more in particular at least 60%, or even at least 70 vol. %. The advantage of providing a large liquid recycle resides in an increased yield of solid acid salt.

The top effluent from the hydrocyclone and the liquid fraction obtained in the solid/liquid separation step both contain dissolved acid salt. The recycle may be directly to the reactor. However, it is also possible to first add other components to the recycle stream, e.g., nutrients or substrate, so that the recycle stream serves as carrier to provide these components to the fermentation reactor. As will be evident to the skilled person there are numerous ways in which the recycle may be effected. Streams may be combined or not, or split or not. The maximum volume to be recycled is not critical. It will depend on reactor volume, and on whether the recycle volume is provided in addition to or instead of volume that will otherwise be provided by pure water. It is preferred for the recycle stream to replace at least in part a corresponding amount of water. As compared to the provision of pure water, as is conventional in fermentation processes, the provision of a solution containing dissolved acid salt means that the fermentation broth will reach the saturation concentration for the acid salt at an earlier stage. This means that per fermentation more solid product will be present in the fermentation broth.

In one embodiment, the recycle fraction provided to the fermentation reactor originating from the solid/liquid separation step and/or from the top effluent from the hydrocyclone, makes up at least 50% of the volume of the broth in the fermentation reactor. At the start of a batch fermentation process a starting liquid is provided to the reactor which comprises the carbohydrate source, sources for nutrients like ammonium, phosphate, and sulphate, and water, to form a liquid medium with the appropriate carbohydrate concentration. Then, the microorganism is added and the medium is brought to fermentation temperature. The fermentation then starts, and base is added to keep the pH at the desired value, as discussed. In one embodiment of the present invention, the starting in the batch process consist for at least 50% of recycled liquid fraction, in particular at least 70%, more in particular at least 80%.

The present invention is particularly attractive for processes carried out on a relatively large scale. For example, it may be preferred for the fermentation medium to have a volume of at least 10.000 liter (10 m$^3$). Much larger volumes may also be envisaged, e.g., at least 50.000 liter (50 m$^3$), or even at least 250.000 liter (250 m$^3$). When operating at this scale the process according to the invention results in substantially increased efficiencies.

It is noted that other steps can be incorporated into the process according to the invention. For example, it is possible to include one or more additional cyclones between the first cyclone and the solid-liquid separation step. These additional cyclones can be used to improve the separation. It is also possible to effect an intermediate washing step between the hydrocyclone and the solid/liquid separation step. Such intermediate washing steps can, e.g., be carried out using washing hydrocyclones, wherein water is added to the effluent from the first hydrocyclone, the combined liquid is provided to a second hydrocyclone, and the bottom effluent from the second hydrocyclone is provided to the solid/liquid fermentation step. The top effluent from such washing hydrocyclone can be processed as desired, e.g., by recycling it to the fermentation step in whole or in part. It is noted that it is preferred to keep the amount of water added in a washing cyclone as limited as possible, to keep the volume streams as small as possible.

The figures illustrate various aspects of the present invention.

In FIG. 1, an effluent if withdrawn from fermentation reactor (1) through line (2), and provided to hydrocyclone (3). The bottom effluent from hydrocyclone (3) is provided through line (4) to solid/liquid separator (5), which is, e.g., a belt filter. The solid product is withdrawn from solid/liquid separator (5) through line (7). The liquid fraction from the solid-liquid separation unit is withdrawn through line (6), and combined with the top effluent from hydrocyclone (3), which is provided through line (8). Of the total effluent stream (6), at least 30 vol. % is recycled to fermentation reactor (1) through line (6a), and a remainder is withdrawn through line (6b).

Figure 2:
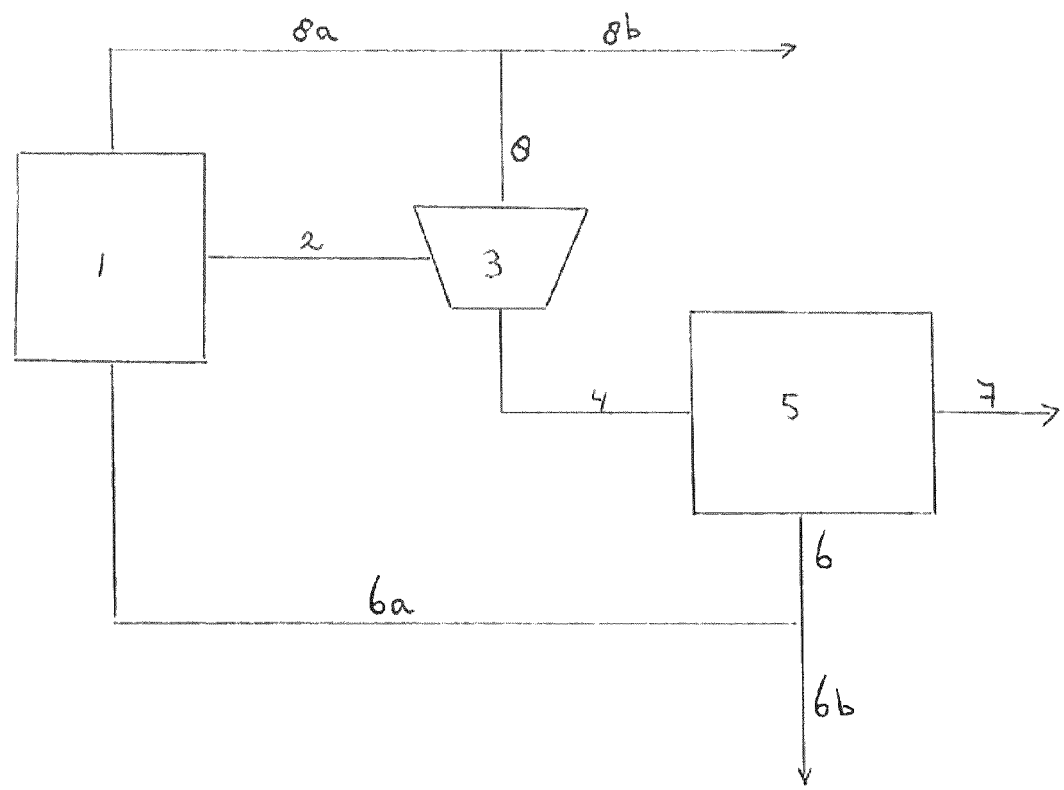
FIG. 2 illustrates a second embodiment of the present invention wherein a few additional possibilities for regulating process streams have been incorporated.

FIG. 2 provides a variation on the process of FIG. 1. In FIG. 2, the recycle of the top effluent stream (8) from the hydrocyclone (3) and the recycle of the liquid fraction (6) from the solid/liquid separator (5) are handled separately, to allow independent selection of the amount of the different fractions that are recycled to the fermentation reactor. More specifically, the top effluent stream (8) is divided into two fractions, one of which is recycled to fermentation reactor (1) through line (8a), and one of which is withdrawn through line (8b). The liquid fraction from the solid-liquid separation unit is withdrawn through line (6), and partly recycled to fermentation reactor (1) through line (6a), while a remainder is withdrawn through line (6b). The process is operated in such a manner that the total the volumes of (6a) and (8a) is at least 30 vol. % of the volume of (6) and (8). It will be evident to the skilled person that many variations are possible on this process. For example, streams (6a) and (8a) may be combined before they are provided to the fermentation reactor.

Figure 3:
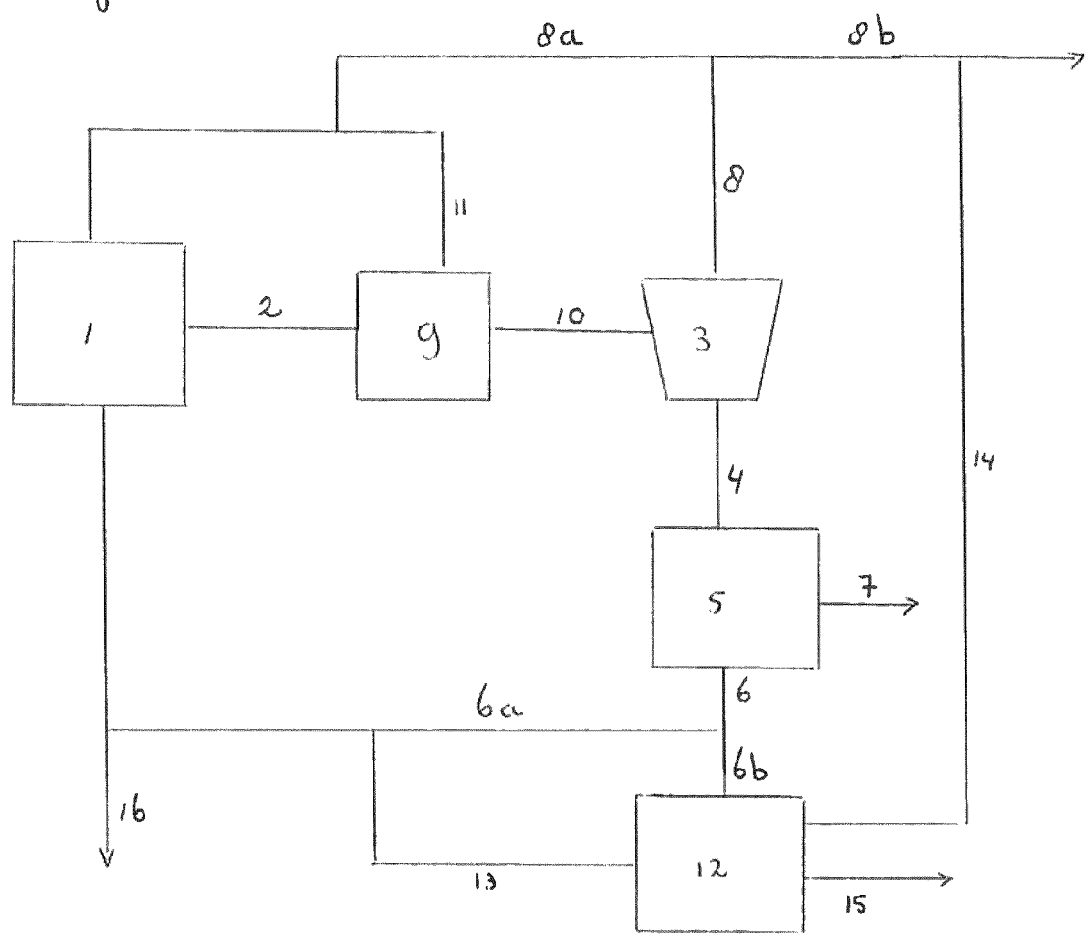
FIG. 3 illustrates a third embodiment of the present invention, in which some additional process steps have been included.

In FIG. 3, the same process is illustrated, with a few additions and modifications. A gravity settler (9) is positioned between fermentation reactor (1) and hydrocyclone (3). The lighter fraction is withdrawn through line (11) and, in the illustrated embodiment, recycled to the fermentation reactor in combination with the top effluent from the hydrocyclone (3). It may of course also be recycled separately, or combined with fraction (6a). The heavy fraction from the gravity settler (9) is provided to the hydrocyclone through line (10).

A further addition is the provision of solidification unit (12), which may, e.g., a crystallizer. In this embodiment at least part of the liquid effluent from the belt filter (5) is provided to the crystallizer, where it is treated under such conditions that acid salt solidifies. If so desired, the effluent stream (8b) may also be provided in whole or in part to the crystallizer (12) through line (14). The solid product formed in the crystallizer (12) is separated of, e.g. through a further solid/liquid separation step (now shown), and withdrawn through line (15). The liquid effluent from the solidification unit (12) is withdrawn through line 13, and, if so desired, recycled at least in part to fermentation unit (1). This can be done, as depicted, by combining it with recycle stream (6a), but it can also be recycled separately. A part of the liquid fraction may be withdrawn through line (16).

It is noted that all additions and variations described in this figure may be applied in the process according to the invention independent from each other. It is noted that the various elements of the various steps of the process according to the invention can be combined as desired.

The present invention is illustrated by the following examples, without being limited thereto or thereby.

Comparative Example A

No Recycle, No Hydrocyclone

A fermentation process was operated in a conventional manner. All of the fermentation broth was withdrawn from the reactor. The fermentation broth contained solid magnesium lactate, and magnesium lactate dissolved in the fermentation medium. The fermentation broth additionally contained biomass, solute contaminants such as potassium salts, sodium salts, residual sugars, oligosaccharides, and sulphate salts, and compounds which are partly in the solid and state and partially dissolved, such as aluminium salts, calcium salts, iron salts, manganese salts, phosphor-containing salts, zinc-containing salts, and nitrogen-containing salts. The effluent is provided to a belt filter. The solid product from the belt-filter has good filtration properties, and an adequate contaminant level. The liquid effluent from the belt-filter is discarded. However, the overall process yield of magnesium lactate was 63%, which is unacceptable from a commercial point of view.

Comparative Example B

Recycle, No Hydrocyclone

Comparative Example A was repeated, except that 55 vol. % of the liquid effluent from the belt filter was recycled to the fermentation reactor in an effort to increase the yield. It was found however, that this resulted in an inoperable process. The solid product from the belt-filter could not be filtered, had a dark-brown colour, and a contaminant level which was unacceptably high. More specifically, the product was found to contain substantial amounts of aluminium, iron, phosphorus and nitrogen.

Comparative Example C

Part Recycle, No Hydrocyclone

Comparative Example B was repeated, except that the percentage of liquid effluent from the belt filter that was recycled was reduced to 26 vol. % in an attempt to improve product properties. The solid magnesium lactate in the bottom effluent from the hydrocyclone has reasonable filtration properties. However, the filter cake still had a brownish color, and an impurity profile which is insufficient for commercial acceptance. The overall yield of the process was 74%, which is also unacceptable for commercial operation.

Example 1

A fermentation process is operated as in Comparative Example A. All of the fermentation broth was withdrawn from the reactor. Its composition is the same as that in Comparative Example A.

The fermentation broth is provided to the hydrocyclone, without any previous processing. The bottom effluent from the hydrocyclone is provided to a belt filter for solid-liquid separation. The solid product is isolated. The top effluent from the hydrocyclone and the liquid fraction from the belt filter are combined, and of the mixture 55 vol. % is recycled to the fermentation reactor.

The solid magnesium lactate in the bottom effluent from the hydrocyclone has good filtration properties and an off-white color. It shows a good impurity profile, as will be discussed below. The overall magnesium lactate yield of the process was 84%, which is sufficient for economic operation.

The following Table shows comparative data on the contaminant profile. The table shows the percentage of contaminant which is present in the liquid phase effluent from the belt filter as compared to the feed provided to the belt filter. Thus, the table provides a measure of the degree of retention of the contaminants on the belt filter. For example, a value of 100% indicates that 100% of a specific component that is provided to a belt filter is present in the liquid effluent from the belt filter, resulting in a retention of 0%.

As can be seen from this table, for the situation where the feed is derived from a hydrocyclone the amount of contaminants present in the belt filter effluent—and thus not in the product—is higher than in the case where the feed is not derived from the hydrocyclone. Thus, the use of a hydrocyclone leads to a product on the belt filter with a higher purity.

| Component | percentage of product in belt filter effluent as compared to product in belt filter feed - process operated without cyclone | percentage of product in belt filter effluent as compared to product in belt filter feed - process operated with cyclone | State of component sol = solid dis = dissolved mix = partly solid/partly dissolved |
|---|---|---|---|
| Aluminum | 84% | 96% | mix |
| Calcium | 95% | 99% | mix |
| Iron | 0% | 17% | mix |
| Potassium | 100% | 99% | dis |
| Manganese | 14% | 22% | mix |
| Sodium | 100% | 100% | dis |
| Phosphor | 47% | 81% | mix |
| Sulfur | 100% | 100% | dis |
| Zinc | 14% | 19% | mix |
| Nitrogen | 82% | 99% | mix |
| total residual sugars | 100% | 100% | dis |
| Polysacharides | 100% | 100% | dis |

The invention claimed is:

1. Fermentation process for the production of an organic acid salt comprising the steps of
    fermenting a carbohydrate source by means of a microorganism in a fermentation medium in a fermentation reactor to form a fermentation broth comprising an organic acid salt, wherein a first part of the organic acid salt is present in the solid state and a remaining part of the organic acid salt is dissolved in the fermentation broth;
    withdrawing at least part of the fermentation broth from the fermentation reactor, providing said withdrawn broth to a hydrocyclone, and withdrawing a top effluent and a bottom effluent from the hydrocyclone;
    providing the bottom effluent from the hydrocyclone to a solid/liquid separation step, to form a solid fraction and a liquid fraction,
    providing at least 30 vol. % of the total of (1) the top effluent from the hydrocyclone and (2) the liquid fraction from the solid-liquid separation step to the fermentation reactor.

2. Fermentation process according to claim 1, wherein at least part of the top effluent from the hydrocyclone is provided to the fermentation reactor.

3. Fermentation process according to claim 1, wherein the organic acid salt is a salt of a carboxylic acid selected from the group consisting of mono-, di-, and tricarboxylic acids having 2-8 carbon atoms.

4. Fermentation process according to claim 3, wherein the carboxylic acid is selected from lactic acid, propionic acid, citric acid, malic acid, maleic acid, fumaric acid, adipic acid, succinic acid, itaconic acid, tartaric acid, alpha-ketoglutaric acid, oxaloacetic acid, acetic acid, acrylic acid, 2-hydroxybutyric acid, 3-hydroxypropionic acid, and furandicarboxylic acid.

5. Fermentation process according to claim 4, wherein the carboxylic acid is selected from the group of lactic acid, succinic acid, fumaric acid, itaconic acid, adipic acid, 3-hydroxypropionic acid, and furan-dicarboxylic acid.

6. Fermentation process according to claim 5, wherein the carboxylic acid is selected from the group of lactic acid, succinic acid, or furandicarboxylic acid.

7. Fermentation process according to claim 1, wherein, of the total amount of organic acid salt in the fermentation broth withdrawn from the fermentation reactor, at least 30% is in the solid state.

8. Fermentation process according to claim 1 wherein of the total amount of organic acid salt in the fermentation broth withdrawn from the fermentation reactor, the amount of solute salt is at least 2 wt. %.

9. Fermentation process according to claim 1, wherein the organic acid salt is a magnesium salt.

10. Fermentation process according to claim 1, wherein the solid/liquid separation step is effected using a belt filter.

11. Fermentation process according to claim 1 wherein at least 50 vol. % of the total of (1) the top effluent from the hydrocyclone and (2) the liquid fraction from the solid-liquid separation step is provided to the fermentation reactor.

12. Fermentation process according to claim 1 wherein the volume of the liquid recycled to the fermentation reactor is at least 50% of the final volume of the broth in the fermentation reactor.

13. Fermentation process according to claim 1, wherein at least 10% of the top effluent is recycled back to the fermentation reactor.

14. Fermentation process according to claim 1 wherein of the liquid fraction from the solid-liquid separation step at least 20 vol. % is recycled to the fermentation reactor, either directly or after intermediate treatment.

15. Fermentation process according to claim 1 wherein the fermentation medium has a volume of at least 10,000 liters.

16. Fermentation process according to claim 1 wherein in the fermentation medium, at least 2% of the organic acid salt is present in the solid state.

17. Fermentation process according to claim 1 wherein in the fermentation medium, at least 5% of the organic acid salt is dissolved in the fermentation broth.

* * * * *